United States Patent [19]

Alkon

[11] Patent Number: 4,570,613
[45] Date of Patent: Feb. 18, 1986

[54] METHOD FOR THE REMOVAL OF SPLINTERS

[76] Inventor: Daniel L. Alkon, 228 Elm Rd., Falmouth, Mass. 02540

[21] Appl. No.: 523,712

[22] Filed: Aug. 15, 1983

[51] Int. Cl.⁴ ............................................. A61B 17/50
[52] U.S. Cl. ................................... 128/1 R; 128/305; 128/355
[58] Field of Search ............... 128/1 R, 355, 305, 304, 128/305.5

[56] References Cited

FOREIGN PATENT DOCUMENTS 327091  6/1903  France ................................. 128/304

*Primary Examiner*—Michael H. Thaler
*Attorney, Agent, or Firm*—Salter & Michaelson

[57] ABSTRACT

A method of removing splinters and the like from the human body includes steps wherein the upper cellular layers of the skin in the area of the splinter are removed by applying substantially unidirectional shaving strokes to the area with a razor-like blade in a direction substantially opposite the direction of insertion of the splinter. After an amount of skin sufficient to expose a portion of the splinter has been removed, continued unidirectional stroking causes the blade to cut slightly into the now exposed splinter to effect the grasping thereof with the blade, whereupon the splinter is extracted by the blade. The preferred apparatus used in performing the method comprises a cutting head, a razor-like blade mounted in the cutting head and an offset handle attached to the cutting head for guiding the apparatus across the skin of a patient to effect shaving strokes in accordance with the method.

1 Claim, 5 Drawing Figures

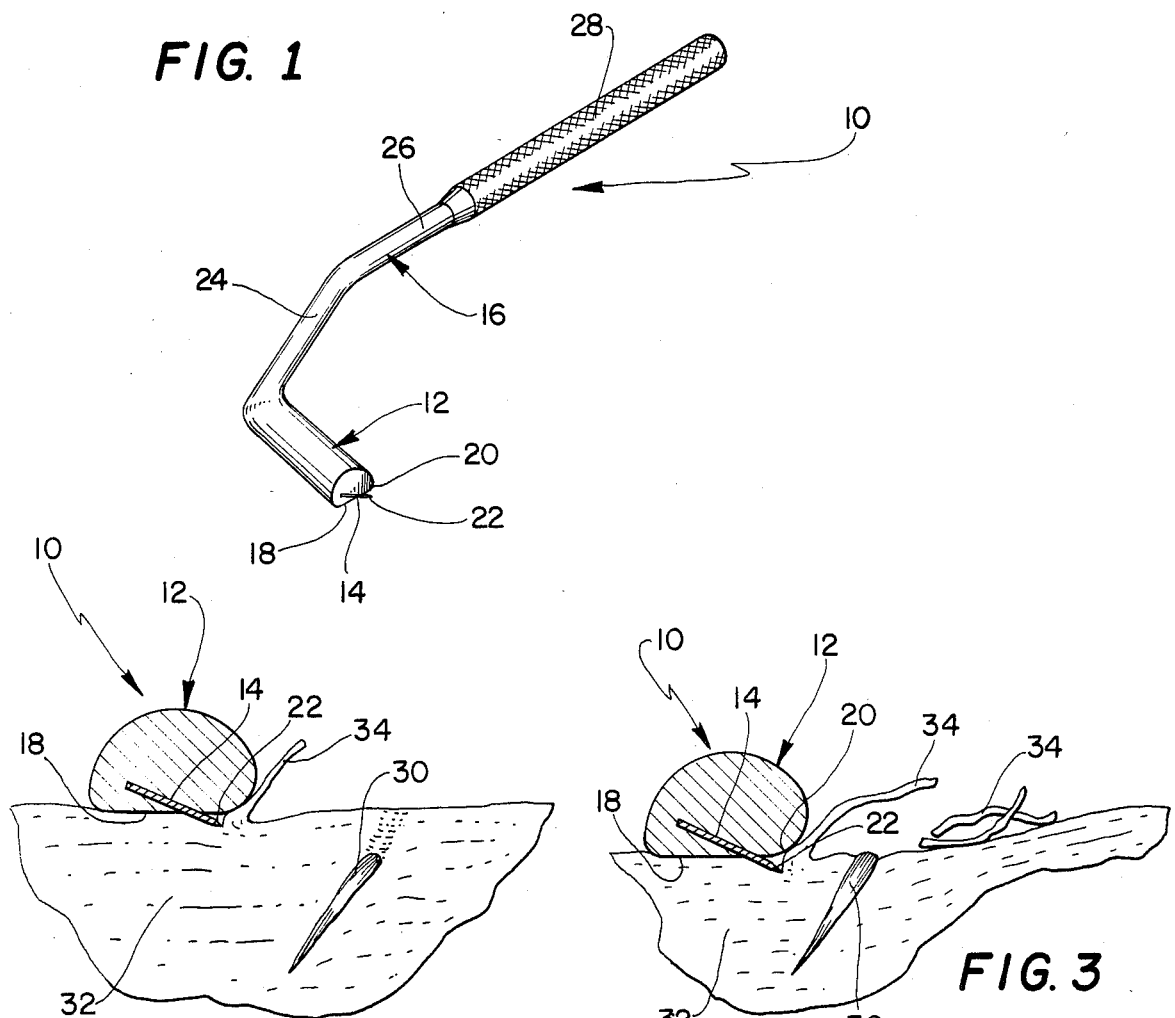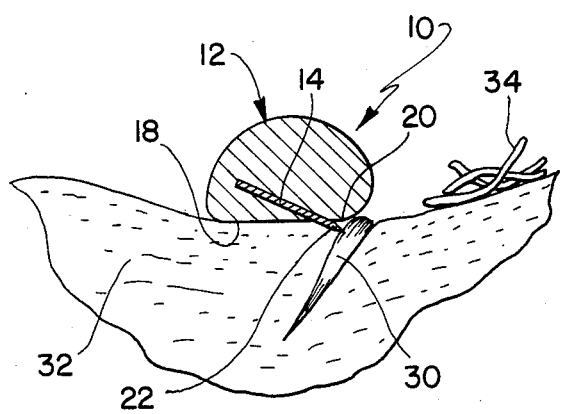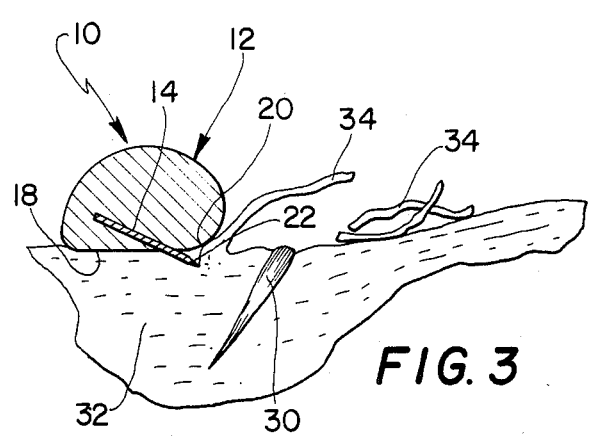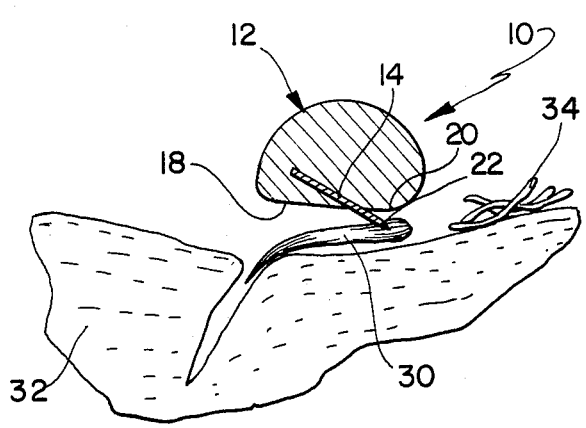

METHOD FOR THE REMOVAL OF SPLINTERS

BACKGROUND AND SUMMARY OF THE INVENTION

The instant invention relates to a method and apparatus for the extraction of splinters and the like from the human body.

Conventional methods for the removal of splinters from the human body have generally comprised operations wherein the splinters are grasped with tweezer-like instruments and pulled therewith to effect the extractions of the splinters. Operations of this type have frequently been very painful and have frequently required the cutting of body tissue is the areas adjacent the splinters in order to gain access to the splinters with the tweezer-like instruments. They have also frequently required painful probing with the tweezer-like instruments in order to effectively grasp the splinters. These probing and cutting procedures have been required particularly in instances wherein splinters are completely embedded beneath the surface of the skin. In most cases conventional tweezers have been used in such methods, although other more sophisticated instruments which operate similar to tweezers but which are specifically adapted for use in the removal of splinters have also heretofore been available. The U.S. patents to Towns U.S. Pat. No. 2,451,994 and Stokes U.S. Pat. No. 4,020,846 disclose instruments which are exemplary in this regard.

The instant invention provides a novel and effective apparatus and method for the removal of splinters with relatively little pain. The method of the instant invention is effected by first shaving the skin in the area where the splinter is imbedded with a razor-like instrument to gradually remove the upper cellular layers of the skin in said area. Preferably this is accomplished by applying substantially unidirectional shaving strokes with the razor-like instrument to the skin in the desired area, the strokes being applied in a direction which is substantially opposite the direction of insertion of the splinter. After the skin in the area of the splinter has been removed sufficiently so that a portion of the splinter is exposed, additional strokes are applied with the razor-like instrument to cause the blade of the instrument to cut slightly into the exposed portion of the splinter to thereby effect a grasping of the splinter, whereupon the splinter may be withdrawn by the instrument.

The method of the instant invention is effective for removing splinters and the like with a minimum of pain to the patient. Specifically, it has been found that little or no pain is involved during the removal of the upper cellular skin layers in the above-described manner; and since the method of the instant invention does not require probing with a tweezer-like instrument, much of the pain associated with the heretofore-known methods for removing splinters is avoided.

The apparatus of the instant invention is constructed for use in during the above-described method and comprises a cutting head having a substantially flat base surface thereon, a razor-like blade which is mounted in the cutting head so that the cutting edge portion of the blade projects from the base surface in the general direction of the leading edge thereof and at an angle to the base surface. An offset handle is attached to the cutting head for manipulating the apparatus, which is operable for removing a splinter by repetitively stroking the apparatus with the base surface thereof in engagement with the patient's skin adjacent the splinter to shave the skin of the patient. It is important to note that the shaving strokes are unidirectional and, specifically, in a direction which is substantially opposite the direction of insertion of the splinter. After the upper cellular layers of the skin have been shaved from the patient so that the splinter is partially exposed, the blade edge engages the splinter to effect the withdrawal thereof in accordance with the method of the instant invention as hereinabove described.

The closest prior art to the apparatus of the instant invention of which the applicant is aware is disclosed in the U.S. patents to Gilhaus et al. U.S. Pat. No. 3,797,505 and Detsch U.S. Pat. No. 4,221,222, both of which relate to medical cutting instruments. However, neither of the devices disclosed in these references is constructed or intended for use in the removal of splinters, and hence the cited references are believed to be of nothing more than general interest.

Accordingly, it is a primary object of the instant invention to provide a method for removing splinters and the like.

Another object of the instant invention is to provide an apparatus for removing splinters and the like in accordance with the method of the instant invention.

Another object of the instant invention is to provide a relatively painless method of removing splinters.

A still further object of the instant invention is to provide an apparatus for removing the upper layers of skin in the area of a splinter and for thereafter graspingly engaging the splinter to effect the withdrawal thereof.

Other objects, features and advantages of the invention shall become apparent as the description thereof proceeds when considered in connection with the accompanying illustrative drawings.

DESCRIPTION OF THE DRAWING

In the drawings which illustrate the best mode presently contemplated for carrying out the present invention:

FIG. 1 is a perspective view of the apparatus of the instant invention;

FIGS. 2 through 5 are sequential sectional views illustrating the operation of the apparatus of the instant invention in carrying out the method of the instant invention to remove a splinter.

DESCRIPTION OF THE INVENTION

Referring now to the drawing, the apparatus of the instant invention is illustrated in FIG. 1 and generally indicated at 10. The apparatus 10 is operable for shaving the upper cellular layers of the skin of a patient in the area adjacent a splinter and for thereafter effecting the removal of the splinter in accordance with the method of the instant invention.

The apparatus 10 comprises a cutting head generally indicated at 12, a cutting blade 14, and a handle portion 16. The cutting head 12 has a substantially flat base surface 18 having a leading edge 20; and the blade 14, which is a razor-like blade having a cutting edge 22, is mounted in the cutting head 12 so that the portion of the blade 14 which includes the cutting edge 22 projects outwardly from the base surface 18 at an acute angle thereto generally in the direction of the leading edge 20. Although in the embodiment of the apparatus of the instant invention herein described and illustrated, the ends of the blade 14 are substantially flush with the ends of the head 12, other embodiments are contemplated wherein the ends of the blade are recessed in the head or covered with projecting caps or the like to avoid having sharp end edges on the blade. The handle 16 comprises a lower portion 24 which extends integrally from the end of head 12 and angles upwardly and then angularly communicates with an upper portion 26, which extends from the lower portion 24 in generally parallel relation to the plane of base surface 18. Provided on the upper portion 26 is a handle grip 28 for facilitating the grasping of the apparatus 10 by an operator. The handle 16 and the cutting head 12 are preferably integrally molded of a transparent plastic material so that an operator of the apparatus 10 can view the area of a patient where cutting is being effected.

The method of the instant invention is sequentially illustrated in FIGS. 2 through 5, the method being carried out by manipulating the apparatus 10 to effect the removal of a splinter 30 from the cellular area 32 of the body of a patient. Although the use of other types of shaving instruments is contemplated, the method of the instant invention is preferably effected using the apparatus 10. In the first step of the method, the apparatus 10 is placed with the base surface 18 in engagement with the upper surface of the skin in the area 32 and by thereafter pulling the handle 16 so that the cutting head 12 is drawn across the surface of the skin in the area 32. As the apparatus 10 is manipulated in this manner, the cutting edge 22 of the blade 14 engages the upper cellular layers of the skin in the area 32 to effect the shaving thereof, whereby shavings 34 are produced. For the most effective performance of the method of the instant invention this shaving operation is effected by repeatedly applying substantially unidirectional strokes to the skin in the area 32 with the apparatus 10, the strokes being applied in a direction which is substantially opposite the direction of insertion of the splinter 30. As the skin in the area 32 is gradually shaved away in the manner illustrated, the outer portion of the splinter 30 is gradually exposed. Thereafter, the apparatus 10 is again drawn over the skin in the area 32 in a direction which is substantially opposite the direction of insertion of the splinter 30 to cause the grasping engagement of the cutting edge 22 with the splinter 30. Specifically, when the cutting edge 22 is drawn over the area 32, it engages the splinter 30 so that it penetrates or cuts slightly thereinto to effect a grasping of the splinter 30, as illustrated most clearly in FIG. 4. Thereafter, the apparatus 10 is further advanced in a direction which is substantially opposite the direction of insertion of the splinter 30 to cause the splinter 30 to be extracted from the cellular area 32 as illustrated in FIG. 5. It should be pointed out that this operation is made possible because a splinter such as the splinter 30 is not rooted in the area 32 such as would be the case with bodily hair; and therefore the tissue in the area 32 does not normally cause significant resistance to the removal of the splinter 30. Hence, when the blade 14 engages the splinter 30, it does not normally sever it but only cuts into it an amount sufficient to effect a grasping thereof, whereupon the splinter 30 can be removed in the manner hereinabove described.

It is seen, therefore, that the instant invention provides an effective method and apparatus for the removal of splinters and the like from the human body. By applying unidirectional strokes with the apparatus 10 to the area 32 adjacent the splinter 30, the upper cellular layers of the skin in the area 32 are actually gradually removed. It has been found that this shaving of the skin to gain access to the splinter 30 is relatively painless, particularly since it is really only the upper cellular skin layers which are removed. After the outer portion of the splinter 30 has been exposed, it can be easily extracted with the apparatus 10 in the manner hereinabove described. Consequently, the splinter 30 is removed without the substantial cutting and/or probing in the area 32 such as was characteristic of the heretofore known methods for removing splinters. Accordingly, it is seen that the method and apparatus of the instant invention represent significant advancements in the medical art for which there is wide application.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A method of removing a splinter or the like from a human body, wherein said splinter has penetrated into the skin of said body so that it is totally unexposed comprising:
    a. shaving the skin of said body in the area thereof adjacent said splinter with a razor-like instrument to remove portions of said skin in said area adjacent said splinter and to thereby partially expose said splinter, said shaving being effected by applying substantially unidirectional strokes with said blade in a direction which is substantially opposite the direction of insertion of said splinter;
    b. cutting into said partially exposed splinter with said blade to effect a grasping thereof with said blade without severing said splinter, said cutting step being effected by moving said blade in substantially the same direction as in said shaving step; and
    c. withdrawing said splinter with said blade by further moving said blade in substantially the same direction as in said shaving step.

* * * * *